United States Patent [19]

Zheng et al.

[11] Patent Number: 5,449,790

[45] Date of Patent: Sep. 12, 1995

[54] PREPARATION OF 10-DEACETYLBACCATIN III AND 7-PROTECTED-10-DEACETYLBACCATIN III DERIVATIVES FROM 10-DEACETYL TAXOL A, 10-DEACETYL TAXOL B, AND 10-DEACETYL TAXOL C

[75] Inventors: Qun Y. Zheng, Superior; Christopher K. Murray, Boulder, both of Colo.

[73] Assignee: Hauser Chemical Research, Inc., Boulder, Colo.

[21] Appl. No.: 224,005

[22] Filed: Apr. 6, 1994

[51] Int. Cl.⁶ ............................................. C07D 305/14
[52] U.S. Cl. ................................. 549/214; 549/510; 549/511
[58] Field of Search ........................ 549/510, 511, 214

[56] References Cited

U.S. PATENT DOCUMENTS

| | | | |
|---|---|---|---|
| 4,857,653 | 8/1989 | Colin et al. | 549/511 |
| 4,924,011 | 5/1990 | Denis et al. | 549/510 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,202,448 | 4/1993 | Carver et al. | 549/510 |
| 5,254,580 | 10/1993 | Chen et al. | 514/449 |
| 5,256,801 | 10/1993 | Carver et al. | 549/510 |

OTHER PUBLICATIONS

Mangatal et al., "Tetrahedron", vol. 45, No. 13, 1989, pp. 4177 to 4190.
Magri et al., "J. Org. Chem.", vol. 51, No. 16, pp. 3239–3242, 1986.
"Modified Taxols. 3. Preparation and Acylation of Baccatin III," by Magri, et al., J. Org. Chem. 1986, 51, 797–802.
"The Chemistry of Taxanes: Reaction of Taxol and Baccatin Derivatives with lewis Acids in Aprotic and Protic Media," by Chen, et al., Tetrahedron vol. 49, No. 14, pp. 2805–2828, 1993.

*Primary Examiner*—Alan L. Rotman
*Assistant Examiner*—Ba K. Trinh
*Attorney, Agent, or Firm*—Steven C. Petersen; Chrisman, Bynum & Johnson

[57] ABSTRACT

The present invention relates to a process for converting purified, partially purified or crude taxane mixtures into a protected precursor of 10-deacetylbaccatin III and into 10-deacetylbaccatin III. The process comprises three steps, the first of which includes contacting a mixture containing at least one naturally occurring taxane compound having the structure (II)

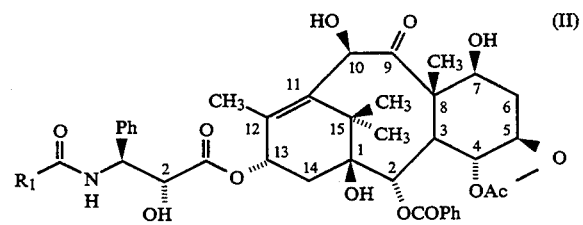

in which $R_1$ is phenyl,

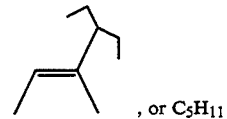

, or $C_5H_{11}$

[an ester linkage at the C-13 position] with at least one hydroxy protecting group. The second step involves cleaving the ester linkage of the protected taxane thus giving rise to a protected precursor of 10-deacetylbaccatin III, the deprotection of which leads to 10-deacetylbaccatin III.

13 Claims, No Drawings

PREPARATION OF 10-DEACETYLBACCATIN III AND 7-PROTECTED-10-DEACETYLBACCATIN III DERIVATIVES FROM 10-DEACETYL TAXOL A, 10-DEACETYL TAXOL B, AND 10-DEACETYL TAXOL C

BACKGROUND OF THE INVENTION

1. Field of the Invention

The present invention relates to a process for converting purified, partially purified or crude taxane mixtures into a protected precursor of 10-deacetylbaccatin III or into 10-deacetylbaccatin III. Specifically, the present invention relates to a three-step process whereby in the first step the 2'-OH and the 7-OH groups of 10-deacetyl taxol A, B or C are protected using a suitable protecting group. Cleavage of the side chain located at the C-13 position occurs during the second step of the process resulting in a protected precursor of 10-deacetylbaccatin III. Deprotection occurs during the third step resulting in 10-deacetylbaccatin III.

2. Description of the State of Art

Between the years 1958 and 1980, extracts of over 35,000 plant species were tested for anticancer activity as part of an NCI-sponsored program. Chemists Monroe E. Wall and M. C. Wani first isolated a crude extract concentrate from yew tree (Taxus brevifolia) bark and wood samples in 1963. Initial screening showed the extract to be a potential anticancer agent, being very active against an unusually wide range of rodent cancers. Isolation of the active agent in the crude extract took several years due to the very low concentrations of the agent present in the plants. The active agent was identified, the structure determined and the compound was named taxol (I), in 1971.

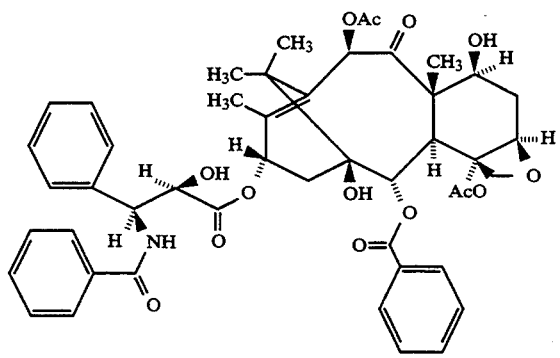

Despite taxol's excellent activity in model tumor systems, clinical trails were delayed owing to short supplies of the drug and formulation problems related to the drug's low water solubility. However, great interest in the drug was rekindled when it was discovered in 1979 by Susan B. Horwitz and co-workers that a unique mechanism for taxol's antitumor activity involved cell microtubules. See, Nature 277:665-667 (1979). Microtubules play a key role in mitosis, maintenance of cell shape, cell motility, and intracellular transport. They are self-assembling and self-disassembling structures that are in dynamic equilibrium with tubulin dimers, the protein subunits of which they are composed. A substance that interferes with microtubules can disrupt cell growth and function.

The 1979 study by S. Horwitz et al., reported that the binding of taxol to tubulin acts to stabilize cell microtubules and to prevent their depolymerization. Thus, taxol increases the time required for cell division which in turn inhibits tumor activity. Discovery of this unique mechanism, by which taxol disrupts the proliferation of cancerous cells, intensified research interest in the drug, and the National Cancer Institute (NCI) began a concerted effort to obtain taxol for clinical trials. In ongoing clinical trials, taxol has shown promising results in fighting advanced cases of ovarian, breast, and other cancers. Recently, taxol was approved by the Food and Drug Administration for the treatment of refractory ovarian cancer; however, taxol is extracted in limited quantities from a natural vegetation that is in short supply.

There have been some methods developed for increasing the supply of taxol. For example, tissues of Taxus brevifolia have been successfully cultured to produce taxol, related alkaloids, and alkaloid precursors, as disclosed in U.S. Pat. No. 5,019,504 issued to Christen et al. Turning toward an alternative route, Holton et al., JACS 110:6558 (1988) proposed a synthetic route, directed to the synthesis of the tetracyclic taxane nucleus from commodity chemicals. Despite the progress made in this approach, the final total synthesis of taxol is, nevertheless, likely to be a multi-step, tedious, and costly process.

An alternate approach to the total synthesis of taxol has been a partial synthesis or semi-synthetic route, involving the use of related alkaloid precursors, collectively referred to as taxanes. U.S. Pat. No. 4,924,011 issued to Denis et al., discloses a process whereby taxol is prepared from a derivative of 10-deacetylbaccatin III or baccatin III. The U.S. Pat. No. 4,857,653 issued to Colin et al. discloses processes for the preparation of taxol and 10-deacetyl taxol from baccatin III and 10-deacetylbaccatin III, respectively. Carver et al., in his U.S. Pat. No. 5,202,448, discloses a method whereby partially purified mixtures of taxanes containing taxol and cephalomannine are converted into baccatin III.

The above U.S. patents and technical paper by Holton each disclose a process whereby the supply of taxol may be increased; however, the amount of taxol actually produced by way of tissue cultures as disclosed by Christen et al. is minute, and although 10-deacetyl taxol is known to promote in vitro the polymerization of tubulin and to inhibit, at the same time, the depolymerization of microtubules, the only taxane currently approved for use as a chemotherapeutic agent is taxol. Consequently, other naturally occurring taxanes that are similar in structure such as 10-deacetyl taxol are useful and valuable only if they can be ultimately converted to taxol. The semi-synthetic route disclosed in the Denis et al. patent is unfortunately limited by the precursors required for the starting material. The Carver et al. patent addresses this need by disclosing a process whereby baccatin III, a precursor for the semi-synthetic route may be obtained. However, the use of sodium borohydride as a reducing salt resulted in an undesired epimerization at the C-7 position, decreasing the yield of baccatin III. To counteract the epimerization event at the C-7 position, Carver et at. discloses the use of Lewis acids. The heavy metal halides used are extremely toxic and it would be undesirable to introduce this type of toxic into a process for a pharmaceutical drug.

There is still a need, therefore, for a process to convert other naturally occurring taxanes to taxol or to taxol precursors that can be easily converted into taxol.

SUMMARY OF THE INVENTION

Accordingly, it is an object of this invention to provide a method to convert partially purified or crude taxane mixtures into 10-deacetylbaccatin III.

Another object of the present invention is to provide a method to convert partially purified or crude taxane mixtures into 7-protected-10-deacetylbaccatin III.

Another object of the present invention is to provide a method to convert selected pure taxanes into 10-deacetylbaccatin III.

A further object of the present invention is to provide a method to convert selected pure taxanes into 7-protected-10-deacetylbaccatin III.

Additional objects, advantages and novel features of this invention shall be set forth in part in the description and examples that follow, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein the method of this invention comprises contacting a mixture containing at least one taxane compound having an ester linkage at the C-13 position with a hydroxy protecting group and then cleaving the ester linkage resulting in a taxol intermediate having the hydroxyl group positioned at C-7 protected, the deprotection of which furthermore leads to a known taxol intermediate.

DETAILED DESCRIPTION OF THE PREFERRED EMBODIMENT

The present invention relates to a high yield process for converting purified, partially purified or crude mixtures of naturally occurring taxanes containing 10-deacetyl taxol A, 10-deacetyl taxol B, or 10-deacetyl taxol C into 7-protected-10-deacetylbaccatin III and 10-deacetylbaccatin III.

The structure of 10-deacetyl taxol A (II)

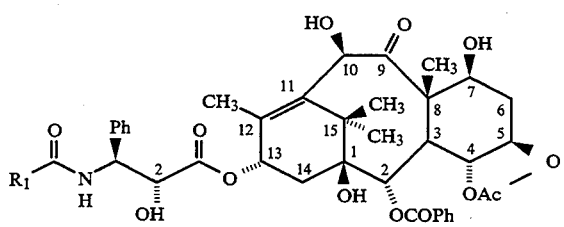

has the basic structure of taxol with $R_1 = Ph$. The structures of 10-deacetyl taxol B and C are similar to formula (II) above except that

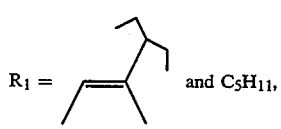

respectively.

The structure of 10-deacetylbaccatin III (III)

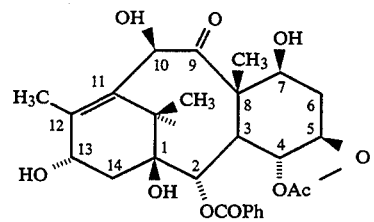

has the basic diterpenoid structure of taxol without the side chain at the C-13 position. The structure of 7-Protected-10-deacetylbaccatin III is similar to the general formula (III) above except the hydroxyl group at the C-7 position is protected.

The preferred embodiment of the present invention requires three steps. The first step includes contacting a solution containing the general formula (II) with a protecting group, thus leading to the protection of the hydroxyl groups located at the C-7 and C-2' positions. The second step includes contacting the resulting 2',7-protected-10-deacetyl taxol A, B or C, with an ester cleavage agent to effectively cleave the ester linkage at the C-13 position resulting in the general formula (III) having the hydroxyl group at the C-7 position being protected. The third and final step includes reacting the product obtained from the preceding step with a deprotecting agent resulting in the deprotection of the hydroxyl group located at the C-7 position which gives rise to the final product of 10-deacetylbaccatin III.

This invention includes a process for the preparation of 10-deacetylbaccatin III and 7-protected-10-deacetylbaccatin III derivatives from purified, partially purified or crude mixtures of 10-deacetyl taxol A, 10-deacetyl taxol B and 10-deacetyl taxol C. The following description will only make reference to 10-deacetyl taxol A; however, it is to be understood, as supported by the Examples which follow, that with each and every occurrence of the term 10-deacetyl taxol A it is contemplated that 10-deacetyl taxol B, 10-deacetyl taxol C or any mixtures thereof may be substituted. The first step in the process, protection of the C-7 and C-2' positioned hydroxyl groups of 10-deacetyl taxol A, is preferably accomplished by contacting, at 0°-25° C. overnight, a purified solution of 10-deacetyl taxol A with a protecting group, such as triethylsilyl chloride. In one example of the process the protecting group triethylsilyl chloride ($Et_3SiCl$) is employed due to its stability, cost, and ease in use and removal. Furthermore, protection of the hydroxyl group at the C-7 position eliminates concern of epimerization as discussed in the background section above. However, a variety of protecting groups for the hydroxyl groups and synthesis thereof may be found in "Protective Groups in Organic Synthesis" by T. W. Green, John Wiley and Sons, 1991.

The preferred next step in the process is the basic hydrolysis or reduction of the ester linkage at the C-13 position, resulting in the general formula (III), with the hydroxyl group at the C-7 position being protected. Reduction of an ester in base is an extremely efficient and irreversible reaction. As such, reduction often gives better yields of carboxylic acids and alcohol than does acid hydrolysis. In this preferred second step 2', 7-protected-10-deacetyl taxol A is reacted with sodium borohydride, at room temperature, for twenty-four hours resulting in the cleavage of the ester linkage at the C-13 position producing 7-protected-10-deacetylbaccatin III, having general formula (III), or 7-Et₃Si-10-deacetylbaccatin III. The conversion does not result in a significant loss of any of the 7-Et₃Si-10-deacetylbaccatin III. Furthermore, the 7-Et₃Si-10-deacetylbaccatin III has potential commercial value as an intermediate in the synthesis of taxol. The specific protecting group used only has to be compatible with the chemical conversion used in this process.

The preferred final step in the process of the present invention, deprotection of the C-7 positioned hydroxyl group of 7-Et₃Si-10-deacetylbaccatin III, is accomplished by reacting a weak acid, such as 1% HCl/MeOH, at 0° C. for three hours with the compound 7-Et₃Si-10-deacetylbaccatin III to produce 10-deacetylbaccatin III.

In the second embodiment of the present invention the hydrolysis step described previously is accomplished by contacting 2', 7-protected-10-deacetyl taxol A with an aqueous solution of NaOH, at room temperature, for twenty-four hours.

In the third embodiment of the present invention the hydrolysis step described in the preferred embodiment is accomplished by contacting 2', 7-protected-10-deacetyl taxol A with a solution of NH₃/MeOH, at room temperature, for twenty-four hours.

In the fourth embodiment of the present invention the hydrolysis step described in the preferred embodiment is accomplished by contacting 2', 7-protected-10-deacetyl taxol A with a Lewis acid, such as, cesium fluoride or lithium iodide, at room temperature overnight.

In the fifth embodiment of the present invention a crude mixture of 10-deacetyl taxol A is converted into both 7-protected-10-deacetylbaccatin III and 10-deacetylbaccatin III as described in the prior three embodiments.

The following non-limited examples provide specific high yield processes for preparing 7-protected-10-deacetylbaccatin III and 10-deacetylbaccatin from purified, partially purified or crude mixtures of manes containing 10-deacetyl taxol A, 10-deacetyl taxol B or 10-deacetyl taxol C. All scientific and technical terms have the meanings as understood by one with ordinary skill in the art. ¹H and ¹³C NMR spectra were recorded on a Varian Gemini-400 instrument. The chemical shifts are expressed in ppm relative to the reference of CDCl₃ or DMSO. Deuterated solvents were purchased from Aldrich Chemical Co. IR was measured on a KVB Analect Diamond-20 FT-IR Spectrometer featuring a Laser Precision XAD-Plus Microscope. Electrospray mass spectra were obtained from a VG Platform HPLC-MASS Spectrometer. TLC plates of silica gel 60F254 were purchased from E.M. Merck and kept in a closed container over Drierite® prior to use. Melting points were measured on a MEL-TEMP II apparatus equipped with a digital Burnant 100 Thermocouple Thermometer and are uncorrected. HPLC was performed on a Hitachi chromatographic spectrometer (L-6200A Intelligent Pump, D-600 Interface, L-4000 UV Detector and AS-4000 Intelligent Auto Sampler). Combination of CH₃CN and H₂O in different concentrations are used as HPLC solvent system. All solvents were distilled before use. Commercially available chemicals were used without any further purification. Various methods of purifying the products of the present invention are known and understood by those skilled in the art and the purification methods presented in the Examples is solely listed by way of example and is not intended to limit the invention.

EXAMPLE I

A. Preparation of 2', 7-Bis(Et₃Si)-10-DAT 62 mg (0.08 mmol) of 10-deacetyl taxol A and 2 ml of pyridine were introduced under an argon atmosphere into a 25 ml round bottomed flask equipped with a magnetic stir bar. 300 μl (20-eq) of triethylsilyl chloride was added via a syringe. The mixture was then stirred at room temperature for twenty-four hours.

A few drops of water were then added to the mixture. The reaction mixture presumed to contain 2', 7-Bis(Et₃Si)-10-DAT was extracted twice using methylene chloride and water (50:50 by volume). The organic phase was collected, dried over anhydrous magnesium sulfate and subsequently filtered. The solvent was removed under reduced pressure to obtain a colorless oil as crude product. The crude product was purified by flash column chromatography on silica gel and eluting with 25% ethylacetate/hexane. The selected fractions were evaporated to dryness with a rotary evaporator under reduced pressure. 79 mg of 2', 7-Bis(Et₃Si)-10-DAT were recovered resulting in a 99% yield. TLC: silica gel, Rf=0.23 for 2', 7-Bis(Et₃Si)-10-DAT at 7% methanol/methylene chloride solvent system. The compound is identical to the known compound.

B. Side Chain Cleavage to form 7-Et₃Si-10-DAB 0.138 ml of an (1.34M, 1-eq) ammonium/methanol solution and 0.8 ml of methanol was added to a 4 ml vial, equipped with a magnetic stir bar, having 11.3 mg (0.011 mmol) of 2', 7-Bis(Et₃Si)-10-DAT. The reaction was stirred at room temperature for twenty hours and the solvent was removed under reduced pressure. The residue was redissolved in methylene chloride and the resulting organic solution was then extracted twice with 20 ml methylene chloride/water (50:50 by volume). The organic phase was collected and dried over anhydrous magnesium sulfate. The solvent was then evaporated under reduced pressure to obtain 7-Et₃Si-10-DAB as a major product and the side chain as a by product. The proton nuclear magnetic resonance spectrum (400 MHz; deuterated chloroform; chemical shift in ppm; coupling constants J in Hz): ¹H NMR (400 MHz, CDCl₃) δ8.0855 (d, J=7.68 Hz, 2H), 7.5773 (t, J=7.2 Hz, 1H), 7.4485 (t, J=7.2 Hz, 2H), 5.5793 (d, J=6.9 Hz, 1H), 5.1459 (d, J=1.52 Hz; 1H), 4.9415 (dd, J=8.7, 0.5 Hz, 1H), 4.8304 (bm, 1H), 4.3791 (dd, J=10.4, 6.6 Hz, 1H), 4.2973 (d, J=8.48 Hz, 1H), 4.2478 (d, J=1.56 Hz, 1H), 4.1434 (d, J=8.44 Hz,1H, 3.9285 (d, J=7.0, Hz, 1H), 2.4250 (d, 1H), 2.2595 (s, 3H), 2.2425 (dd, 1H), 2.2252 (dd, 1H), 2.1200 (m, 1H), 2.0528 (s, 3H), 1.8655 (ddd, 1H), 1.7054 (s, 3H), 1.6415 (bs, 1H), 1.24505 (bs, 1H), 1.0483 (s, 3H), 1.0483 (s, 3H), 0.9082 (t, J=7.96, Hz, 9H), 0.5264 (m, 6H). MS (electrospray m/e calculated for C₃₅H₅₁O₁₀Si: 658 found 659.1(M+H)⁺. TLC: Rf=0.32 using 5% methanol/methylene chloride solvent system, chromatography purity: 90.4%. The proton NMR and melting point of the product matched the previously reported literature values for 7-Et₃Si-10-DAB, reported by A. E. Greene, "A Highly Efficient, Practiced Approach to Taxol", J. Am. Chem. Soc., 1988, 110:5917–5919, 1988.

C. Deprotection of 7-Et₃Si-10-DAB 25.3 mg (0.038 mmol) of 7-Et₃Si-10-DAB, 1 ml methylene chloride and 1 ml methanol are introduced into a 25 ml round bottomed flask equipped with a magnetic stir bar which was placed at 0° C. (ice bath). A 0.5 ml solution of 1% hydrochloric acid (39%) in methanol was then added to the mixture and stirred at 0° C. for 3 hours.

The solution was then diluted with the addition of 10 ml methylene chloride and extracted twice with 20 ml of saturated sodium bicarbonate, water. The organic layer was then dried over anhydrous magnesium sulfate after. Following the removal of 15.4 mg of 10-DAB was obtained as a major product having a 72% yield. The proton NMR and melting point of the product matched the previously reported literature values for 10-DAB.

EXAMPLE II

A. Preparation of 2', 7-Bis($Et_3Si$)-10-DAT

Prepared in the same manner as described above in Example I.

B. Side Chain Cleavage to form 7-$Et_3Si$-10-DAB 1 ml of methylene chloride/methanol (50:50 by volume) and 5 mg of sodium borohydride was added to a 4 ml vial, equipped with a magnetic stir bar, having 4.6 mg (0.005 mmol) of 2', 7-Bis($Et_3Si$)-10-DAT. The reaction was stirred at room temperature overnight and the solvent was removed under reduced pressure. The residue was redissolved in methylene chloride and the resulting organic solution was then extracted twice with 20 ml methylene chloride/water (50:50 by volume). The organic phase was collected and dried over anhydrous magnesium sulfate. The solvent was then evaporated under reduced pressure to a obtain a crude product. The resulting product proved to be identical to that obtained in Example I above, as analyzed by TLC and HPLC.

C. Deprotection of 7-$Et_3Si$-10-DAB

The procedure for deprotection set out in Example I above was followed.

EXAMPLE III

A. Preparation of 2', 7-Bis($Et_3Si$)-10-DAB

Prepared in the same manner as described above in Example I.

Side Chain Cleavage to form 7-$Et_3Si$-10-DAB 0.5 ml of methanol and 10 drops of a 1% solution of sodium hydroxide was added to a 4 ml vial, equipped with a magnetic stir bar, having 5.0 mg (0.500 mmol) of 2', 7-Bis($Et_3Si$)-10-DAT. The reaction was stirred at room temperature for four hours and the solvent was removed under reduced pressure. The residue was redissolved in methylene chloride and the resulting organic solution was then extracted twice with 20 ml methylene chloride/water (50:50 by volume). The organic phase was collected and dried over anhydrous magnesium sulfate. The solvent was then evaporated under reduced pressure to obtain a crude product. The resulting product proved to be identical to that obtained in Example I above, as analyzed by TLC and HPLC.

C. Deprotection of 7-$Et_3Si$-10-DAB

The above procedure for deprotection set out in Example I above was followed.

EXAMPLE IV

A. Preparation of 2', 7-Bis($Et_3Si$)-10-DATB 24 mg (0.03 mmol) of Deacetyl taxol B and 0.5 ml of pyridine were introduced into a 25 ml round bottomed flask equipped with a magnetic stir bar. 60.0 μl (12eq) of triethylsilyl chloride was added under an argon atmosphere at 0° C. The mixture was then stirred at room temperature for twenty-four hours.

A few drops of water were then added to the mixture. The reaction mixture presumed to contain 2', 7-Bis($Et_3$Si)-10-DATB was extracted twice using methylene chloride and water (50:50 by volume). The organic phase was collected, dried over anhydrous magnesium sulfate and subsequently filtered. The solvent was removed under reduced pressure to obtain a colorless oil as crude product. The crude product was purified by flash column chromatography on silica gel and eluting with 25% ethylacetate/hexane. The selected fractions were evaporated to dryness with a rotary evaporator under reduced pressure. 24.2 mg of 2', 7-Bis($Et_3Si$)-10-DATB were recovered resulting in a 78.2% yield. TLC silica gel, Rf=0.24 for 2', 7-Bis($Et_3Si$)-10-DATB at 25% ethylacetate/hexane solvent system and Rf=0.67 for 2', 7-Bis($Et_3Si$)-10-DATB at 7% methanol/methylene chloride solvent system. The portion nuclear magnetic resonance spectrum (400 MHz; deuterated chloroform; chemical shift in ppm; coupling constants J in Hz); 1H NMR (400 MHz, CDCL3) d, 8.11 (d, J=8.0 Hz, 2H), 7.57 (t, J=8.0 Hz, 1H), 7.48 (t, J=8.0 Hz, 2H), 7.34 (t, J=8.0 Hz, 2H), 7.26 (d, J=8.0 Hz, 4H), 6.68 (d, J=8.0 Hz, 1H), 6.42 (q, J=8.0 Hz, 1H), 6.27 (t, J=8.0 Hz, 1H), 5.65 (d, J=4.0 Hz, 4H), 5.53 (d, J=4.0 Hz, 1H), 5.09 (d, J=1.8 Hz, 1H), 4.92 (d, J=8.0 Hz, 1H), 4.59 (d, J=2.16 Hz, 1H, 4.38 (dd, J=12.0, 8.0 Hz, 1H), 4.25 (d, J=2.0 Hz, 1H ), 4.20 (d, J=8.0 Hz, 1H, 3.86 (d, J=4.0 Hz, 1H), 2.49 (s, 3H), 2.42 (m, 2H), 2.31 (m, 1H), 2.10 (m, 1H), 1.91 (m, 1H), 1.91 (s, 3H), 1.78 (s, 3H), 1.73 (s, 3H), 1.70 (d, J=8.0 Hz, 3H), 1.61 (s, 1H), 1.55 (m, 2H), 1.23 (s, 6H), 1.09 (s, 3H), 0.91 (t, J=8.0 Hz, 9H), 0.78 (t, J=8.0 Hz, 9H), 0.77 (t, 3H), 0.53 (m, 6H), 0.40 (m, 6H); TLC: Rf=0.24, 25% EtOAc/hexane; Rf=0.67, 7% MeOH/$CH_2Cl_2$. HPLC: RT=20.52, C18, MeCN/$H_2O$, (40–100%).

B. Side Chain Cleavage to Form 7-$Et_3Si$-10-DAB 3.7 mg (10eq) of sodium borohydride was added to a 4 ml vial, equipped with a magnetic stir bar, having a solution of 10 mg (0.009 mmol) of 7-Bis($Et_3Si$)-10-DAT in 0.5 ml methanol. The reaction was stirred at room temperature for twenty hours and the solvent was removed under reduced pressure. The residue was redissolved in methylene chloride and the resulting organic solution was then extracted twice with 20 ml methylene chloride/water (50:50 by volume). The organic phase was collected and dried over anhydrous magnesium sulfate. The solvent was then evaporated under reduced pressure to obtain 7-$Et_3Si$-10-DAB as a major product and the side chain as a by-product. The resulting product proved to be identical to that obtained in Example I above, as analyzed by TLC and HPLC.

C. Deprotection of 7-$Et_3Si$-10-DAB

The procedure for deprotection set out in Example I above was followed.

EXAMPLE V

A. Preparation of 2', 7-Bis($Et_3Si$)-10-DATC 164 mg (0.20 mmol) of 10-deacetyl taxol C and 4 ml of pyridine were introduced into a 25 ml round bottomed flask equipped with a magnetic stir bar. 0.684 ml (20-eq) of triethylsilyl chloride was added under an argon atmosphere at 0° C. The mixture was then stirred at room temperature overnight.

A few drops of water were then added to the mixture. The reaction mixture presumed to contain 2', 7-Bis($Et_3$Si)-10-DATC was extracted twice using methylene chloride and water (50:50 by volume). The organic phase was collected, dried over anhydrous magnesium sulfate, and subsequently filtered. The solvent was removed under reduced pressure to obtain a colorless oil as crude product. The crude product was purified by flash column chromatography on silica gel using air pressure and eluting with 20% ethylacetate/hexane. The selected fractions were evaporated to dryness with a rotary evaporator under reduced pressure. 155.6 mg of 2′, 7Bis(Et$_3$Si)-10-DAT were recovered resulting in a 82% yield. $^1$H NMR (400 MHz, CDCl$_3$)δ 8.11 (d, J=7.04 Hz, 2H), 7.57 (t, J=7.20 Hz, 1H), 7.48 (t, J=7.24 Hz, 2H), 7.35 (t, J=7.72 Hz, 2H), 7.29 (d, J=7.00 Hz, 1H), 7.25 (d, J=7.12 Hz, 1H), 6.38 (d, J=9.12 Hz, 1H), 6.27 (t, J=8.80 Hz, 1H), 5.66 (d, J=7.20 Hz, 1H), 5.53 (d, J=9.00 Hz, 1H), 4.93 (d, J=7.8 Hz, 1H), 4.57 (d, J=1.96 Hz, 1H), 4.38 (dd, J=10.0, 6.44 Hz, 1H), 4.31 (d, J=8.32 Hz, 1H), 4.26 (d, 1H), 4.21 (d, J=8.68 Hz, 1H), 3.88 (d, J=6.96 Hz, 1H), 2.50 (s, 3H), 2.44 (m, 2H), 2.32 (m, 1H), 2.21 (t, J=8.28 Hz, 2H), 2.12 (m, 1H), 1.91 (s, 3H), 1.90 (m, 1H), 1.86 (s, 1H), 1.78 (s, 1H), 1.74 (s, 3H), 1.54 (m, 3H), 1.24 (m, 8H), 1.10 (s, 3H), 0.92 (t, 9H), 0.78 (t, 9H), 0.53 (m, 6H), 0.40 (m, 6H); FT-IR (neat) 3064.3, 3025.8, 2956.3, 1754.9, 1731.8, 1702.8, 1683.6, 1602.6, 1494.6, 1454.1, 1270.9, 1245.8 cm$^{-1}$; MS (electrospray m/e 1034.4, (M+H)$^+$, 1056.4 (M+Na)$^+$; HPLC: C18 column, CH$_3$CN (40%–100%)/H$_2$O, RT:22.46 min, Chrom. purity: 95.44%.

B. Side Chain Cleavage to form 7-Et$_3$Si-10-DAB 2 ml of methanol, 10 drops of methylene chloride and 18 mg (10 eq) sodium borohydride was added to a 25 ml round bottomed flask, equipped with a magnetic stir bar, having 56.9 mg (0.055 mmol) of 2′,7-Bis(Et$_3$Si)-10-DAT. The reaction was stirred at room temperature for twenty hours and the solvent was removed under reduced pressure. The residue was redissolved in methylene chloride and the resulting organic solution was then extracted twice with 20 ml methylene chloride/water (50:50 by volume). The organic phase was collected and dried over anhydrous magnesium sulfate. The solvent was then evaporated under reduced pressure to a viscous oil as residue. The residue was purified using a silica gel column eluting with a 5% methanol/methylene chloride solution. The selected fractions were then evaporated to dryness under reduced pressure. The dry organic material was then recrystallized from methanol. 24.9 mg of 7-Et$_3$Si-10-DAB were recovered resulting in a 92.3% yield. The proton nuclear magnetic resonance spectrum (400 Hz; deuterated chloroform; chemical shift in ppm; coupling constants J in Hz).

C. Deprotection of 7-Et$_3$Si-10-DAB

The procedure set out in Example I above was followed.

EXAMPLE VI

A. Preparation of 2′, 7-Bis(Et$_3$Si)-10-DATC From the Crude Mixture Which Contains 2.5% 10-DATC 16.2 mg containing approximately 2.5% 10-DATC and 500 μl of pyridine (32 mg/ml) were introduced under a nitrogen atmosphere into a 25 ml round bottom flask equipped with a magnetic stir bar. 4.7 ml (18-eq) of triethylsilyl chloride was added via a syringe. The mixture was then stirred at room temperature overnight.

The mixture was then diluted with methylene chloride and extracted twice with 10% copper sulfate, water and brine. The organic phase was collected, dried over anhydrous magnesium sulfate and subsequently filtered. The solvent was removed under reduced pressure to obtain a colorless oil as a crude product. The crude product was purified by flash column chromatography or silica gel using air pressure and eluting with 25% ethylacetate/hexane. The selected fractions were evaporated to dryness with a rotary evaporator under reduced pressure. 10.6 mg of 2′, 7-Bis(Et$_3$Si)-10-DATC were recovered.

B. Side Chain Cleavage to Form 7-Et$_3$Si-10-DAB

To a 4 ml vial, equipped with a magnetic stir bar, 10.6 mg of 2′, 7-Bis(Et$_3$Si)-10-DATC was added and dissolved in 0.5 ml MeOH. 8.2 mg of sodium borohydride was added and the reaction was stirred at room temperature overnight followed by removal of all solvent under reduced pressure. The residue was redissolved in methylene chloride and the resulting organic solution was then extracted twice with water. The organic phase was collected and dried over anhydrous magnesium sulfate. The solvent was then evaporated under reduced pressure to obtain 8.6 mg of 7-Et$_3$Si-10-DAB as a major product and the side chain as a by product. HPLC analysis indicated a chromatographic purity of 30.2%

C. Deprotection of 7-Et$_3$Si-10-DAB The above procedure for deprotection set out in Example III above was followed.

EXAMPLE VII

A. Preparation of 2′, 7-Bis(Et$_3$Si)-10-DATC From the Crude Mixture Which Contains 7.5% 10-DATC 21.9 mg containing approximately 7.5% 10-DATC and 700 μl of pyridine (31 mg/ml) were introduced under a nitrogen atmosphere into a 25 ml round bottom flask equipped with a magnetic stir bar. 24.8 μl (22-eq) of triethylsilyl chloride was added via a syringe. The mixture was then stirred at room temperature overnight.

The mixture was then diluted with methylene chloride and extracted twice with 10% copper sulfate, water and brine. The organic phase was collected, dried over anhydrous magnesium sulfate and subsequently filtered. The solvent was removed under reduced pressure to obtain a colorless oil as a crude product. The crude product was purified by flash column chromatography or silica gel using air pressure and eluting with 25% ethylacetate/hexane. The selected fractions were evaporated to dryness with a rotary evaporator under reduced pressure. 14.2 mg of 2′, 7-Bis(Et$_3$Si)-10-DATC were recovered.

B. Side Chain Cleavage to Form 7-Et$_3$Si-10-DAB

To a 4 ml vial, equipped with a magnetic stir bar, 14.2 mg of 2′, 7-Bis(Et$_3$Si)-10-DATC was added and dissolved in 0.5 ml MeOH. 12.3 mg of sodium borohydride was added and the reaction was stirred at room temperature overnight followed by removal of all solvent under reduced pressure. The residue was redissolved in methylene chloride and the resulting organic solution was then extracted twice with water. The organic phase was collected and dried over anhydrous magnesium sulfate. The solvent was then evaporated under reduced pressure to obtain 5.5 mg of 7-Et$_3$Si-10-DAB as a major product and the side chain as a by product. HPLC analysis indicated a chromatographic purity of 70.3%

C. Deprotection of 7-Et$_3$Si-10-DAB

The above procedure for deprotection set out in Example III above was followed.

EXAMPLE VIII

A. Preparation of 2′, 7-Bis(Et$_3$Si)-10-DAT

Prepared in the same manner as described above in Example I.

B. Side Chain Cleavage to Form 7-Et$_3$Si-10-DAB 29.4 mg (0.028 mmol) of 2′, 7Bis(Et₃Si)-10-DAT and 640 µl anhydrous methanol were introduced into a 4 ml vial equipped with a magnetic stir bar. 8.8 mg (0.058 mmol, 2 equivalent) of cesium fluoride was added under a nitrogen atmosphere at room temperature. The mixture was then stirred for 5 days.

The reaction mixture was then diluted in ethyl acetate and the resulting organic solution was then extracted twice with 30 ml brine. The organic phase was collected and dried over anhydrous magnesium sulfate. The solvent was then evaporated under reduced pressure to obtain a crude product. The resulting major product proved to be identical to the 7-Et₃Si-10-DAB obtained in Example I above, as analyzed by TLC, MS and HPLC. Methyl ester side chain and 10-DAB were also found as by-products.

C. Deprotection of 7-Et₃Si-10-DAB

The above procedure for deprotection set out in Example I above was followed.

The embodiments of the invention in which an exclusive property or privilege is claimed are defined as follows:

1. A process for the preparation of a compound of structure (I)

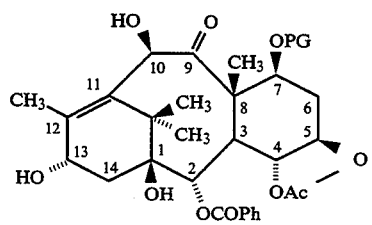

wherein PG = a Protecting Group, comprising the steps of:

protecting the hydroxyl groups at the C-2′ and C-7 positions of at least one naturally occurring taxane compound having the structure (II)

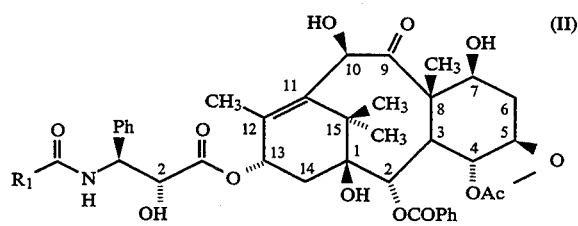

in which R₁ is phenyl, with at least one type of hydroxy protecting group; and cleaving the ester linkage at the C-13 position by contacting said protected taxane compound(s) of structure (II) with at least one alkali solution to form said compound of structure (I).

2. The process of claim 1, further including the step of contacting an acidic solution to said protected taxane compound of structure (I) subsequent to the cleavage step thereby forming a compound of structure (III),

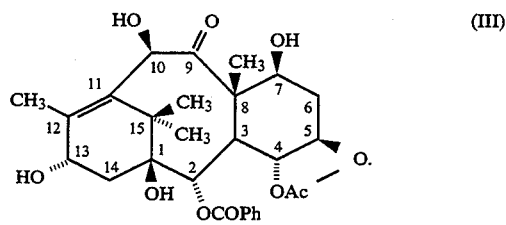

3. The process of claim 1, wherein R₁ is

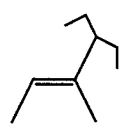

4. The process of claim 1, wherein R₁ is C₅H₁₁.

5. The process of claim 1, wherein said hydroxy protecting group is triethylsilyl chloride.

6. The process of claim 1, wherein said alkali solution is sodium hydroxide.

7. The process of claim 1, wherein said alkali solution is ammonia in methanol.

8. A process for the preparation of a compound of structure (III)

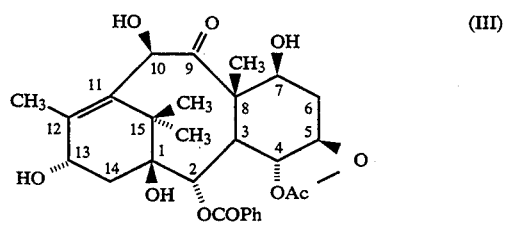

comprising the steps of:

protecting the hydroxyl groups at the C-2′ and C-7 positions of at least one naturally occurring taxane compound having the structure (II)

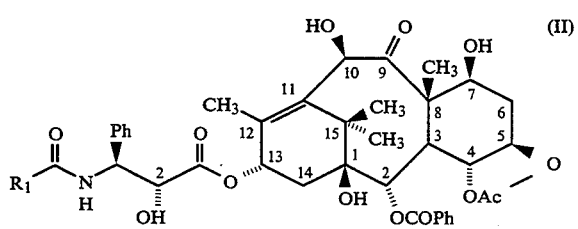

in which R₁ is phenyl, with at least one type of hydroxy protecting group;

cleaving the ester linkage at the C-13 position by contacting said protected taxane compound(s) of structure (II) with at least one alkali solution thereby forming a compound of structure (I)

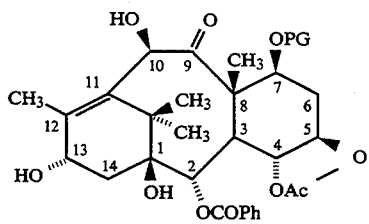 (I)

and;
 deprotecting said hydroxyl group at the C-7 position to form said compound of structure (III).
9. The process of claim 8, wherein $R_1$ is

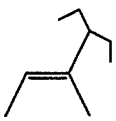

10. The process of claim 8, wherein $R_1$ is $C_5H_{11}$.
11. The process of claim 8, wherein said hydroxy protecting group is triethylsilyl chloride.
12. The process of claim 8, wherein said alkali solution is sodium hydroxide.
13. The process of claim 8, wherein said alkali solution is ammonia in methanol.

UNITED STATES PATENT AND TRADEMARK OFFICE
CERTIFICATE OF CORRECTION

PATENT NO. : 5,449,790
DATED : September 12, 1995
INVENTOR(S) : Zheng et al.

It is certified that error appears in the above-indentified patent and that said Letters Patent is hereby corrected as shown below:

In the abstract, the structure (II), the right-hand side of the formula reading 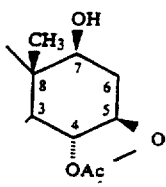 should read 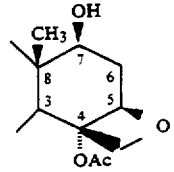

In the abstract, designated line 9, delete "[an ester linkage at the C-13 position]".

In column 3, designated lines 46-55, the right-hand side of the formula;
In column 4, designated lines 1-10, the right-hand side of the formula;

In column 11, designated lines 46-55, the right-hand side of the formula;
In column 12, designated lines 1-10, the right-hand side of the formula;
In column 12, designated lines 35-44, the right-hand side of the formula;
In column 12, designated lines 51-59, the right-hand side of the formula;
all reading:

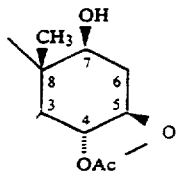 should read 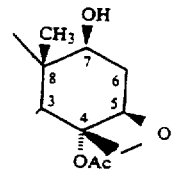

In column 5, designated line 39, delete "manes" and substitute --taxanes--.
In column 6, designated line 3, after "-DAT", insert --:--.

UNITED STATES PATENT AND TRADEMARK OFFICE
CERTIFICATE OF CORRECTION

PATENT NO. : 5,449,790
DATED : September 12, 1995
INVENTOR(S) : Zheng et al.

It is certified that error appears in the above-indentified patent and that said Letters Patent is hereby corrected as shown below:

In column 6, designated lines 26 and 63, after each occurence of "-DAB", insert --:--.

In column 7, designated line 13, after "-DAT", insert --:--.

In column 7, designated lines 16, 32, 40, and 55, after each occurence of "-DAB", insert --:--.

In column 7, designated line 37, delete "-DAB" and insert "-DAT:".

In column 7, designated line 40, before the word "Side", insert --B. --.

In column 7, designated line 60, after "-DATB", insert --:--.

In column 8, designated lines 34 and 50, after each occurence of "DAB", insert --:--.

In column 8, designated line 55, after "-DATC", insert --:--.

In column 9, designated line 6, delete "7Bis" and substitute --7-Bis--.

In column 9, designated lines 26 and 49, after each occurence of "-DAB", insert --:--.

In column 9, designated line 55, after "10-DATC", insert --:--.

In column 10, designated lines 6, 20, 46, 60, and 68, after each occurence of "-DAB", insert --:--.

In column 10, designated line 26, after "-DATC", insert --:--.

In column 10, designated line 65, after "-DAT", insert --:--.

In column 11, designated line 1, delete "7Bis" and substitute --7-Bis--.

In column 11, designated line 20, after "-DAB ", insert --:--.

UNITED STATES PATENT AND TRADEMARK OFFICE
CERTIFICATE OF CORRECTION

PATENT NO. : 5,449,790
DATED : September 12, 1995
INVENTOR(S) : Zheng et al.

It is certified that error appears in the above-indentified patent and that said Letters Patent is hereby corrected as shown below:

In column 11, designated lines 30-39, the right-hand side of the formula; and
In column 13, designated lines 1-10, the right-hand side of the formula, both reading

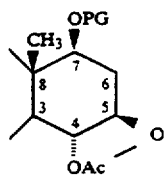 should read 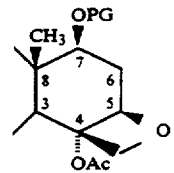

Signed and Sealed this

Seventeenth Day of September, 1996

Attest:

BRUCE LEHMAN

Attesting Officer          Commissioner of Patents and Trademarks